(12) United States Patent
Manjeshwar et al.

(10) Patent No.: US 10,080,540 B2
(45) Date of Patent: Sep. 25, 2018

(54) SYSTEMS AND METHODS FOR EMISSION TOMOGRAPHY/COMPUTED TOMOGRAPHY DATA ACQUISITION (71) Applicants: General Electric Company, Schenectady, NY (US); King's College London, London (GB)

(72) Inventors: Ravindra Mohan Manjeshwar, Glenville, NY (US); Kris Filip Johan Jules Thielemans, London (GB)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 713 days.

(21) Appl. No.: 14/535,947

(22) Filed: Nov. 7, 2014

(65) Prior Publication Data
US 2016/0128664 A1    May 12, 2016

(51) Int. Cl.
*A61B 6/00* (2006.01)
*A61B 6/03* (2006.01)

(52) U.S. Cl.
CPC ............ *A61B 6/5264* (2013.01); *A61B 6/032* (2013.01); *A61B 6/037* (2013.01); *A61B 6/4417* (2013.01);
(Continued)

(58) Field of Classification Search
CPC ....... A61B 6/032; A61B 6/037; A61B 6/4417; A61B 6/5205; A61B 6/5217; A61B 6/5264; A61B 6/541; A61B 6/503; A61B 6/12; A61B 6/5288; A61B 6/504; A61B 6/486; A61B 5/055; A61B 6/481; A61B 6/5247; A61B 5/7289; A61B 6/5235; A61B 2017/00694; A61B 6/027; A61B 6/4441; A61B 6/488; A61B 6/466; A61B 6/482;
(Continued)

(56) References Cited

U.S. PATENT DOCUMENTS 7,574,249 B2    8/2009  Piacsek et al.
8,355,551 B2 *  1/2013  Thielemans .......... G06T 11/005
                                                    378/12
(Continued)

OTHER PUBLICATIONS

Li et al., "Optimizing 4D Cone-beam CT Acquisition Protocol for External Beam Radiotherapy", International Journal of Radiation Oncology Biology Physics, vol. 67, Issue 4, Mar. 15, 2007, pp. 1211-1219.
(Continued)

*Primary Examiner* — Irakli Kiknadze
(74) *Attorney, Agent, or Firm* — GE Global Patent Operation; Pabitra Chakrabarti (57) ABSTRACT

A method includes receiving Emission Tomography (ET) data of a subject from an ET/Computed Tomography (CT) scanner. The method further includes generating a first motion signal corresponding to a first bed position of the ET/CT scanner from the received ET data and determining whether the first motion signal indicates a periodic motion. The method also includes calculating a first time period from the first motion signal in response to determining that the first motion signal indicates the periodic motion and sending a first acquire notification to the ET/CT scanner to acquire Cinematographic (CINE) Computed Tomography (CT) data from the first bed position based on the first time period.

18 Claims, 5 Drawing Sheets

(52) U.S. Cl.
CPC .......... *A61B 6/5205* (2013.01); *A61B 6/5217* (2013.01); *A61B 6/541* (2013.01)

(58) Field of Classification Search
CPC ....... A61B 6/0457; A61B 6/405; A61B 6/469; G06T 2207/30048; G06T 11/60; G06T 2207/10121; G06T 2207/30101; G06T 5/001; G06T 7/0012; G06T 7/0014; G06T 7/13; G06T 7/246; G06T 7/62; G06T 2211/412; G06T 2207/30004; G06T 11/005; G06T 11/008; G06T 11/001; G06T 11/00
USPC ................................. 378/4, 8, 19, 20, 62, 63
See application file for complete search history.

(56) References Cited

U.S. PATENT DOCUMENTS

| | | | |
|---|---|---|---|
| 2004/0258286 A1 | 12/2004 | Salla et al. | |
| 2006/0262958 A1* | 11/2006 | Yin | G06K 9/00771 382/103 |
| 2007/0237289 A1 | 10/2007 | Deller et al. | |
| 2008/0253636 A1 | 10/2008 | Deller | |
| 2009/0123051 A1* | 5/2009 | Tamai | A61B 6/4233 382/132 |
| 2009/0175562 A1* | 7/2009 | Pan | A61B 6/032 382/312 |
| 2009/0216131 A1* | 8/2009 | Chase | A61B 5/0064 600/476 |
| 2010/0063419 A1* | 3/2010 | Mostafavi | A61B 5/1135 600/587 |
| 2011/0116695 A1* | 5/2011 | Wollenweber | A61B 6/469 382/131 |
| 2012/0004518 A1* | 1/2012 | D'Souza | A61B 5/1135 600/301 |
| 2012/0059252 A1 | 3/2012 | Li et al. | |
| 2012/0281897 A1 | 11/2012 | Razifar et al. | |
| 2013/0172730 A1* | 7/2013 | Cohen | A61B 6/12 600/424 |

OTHER PUBLICATIONS

Keall et al., "Respiratory Regularity Gated 4D CT Acquisition: Concepts and Proof of Principle", Australasian Physical & Engineering Sciences in Medicine, vol. 30, Issue 3, 2007, pp. 211-220.
Li et al., "4D CT Sorting Based on Patient Internal Anatomy", Physics in Medicine and Biology, vol. 54, 2009, pp. 4821-4833.
Pourmoghaddas, "Respiratory Motion-Compensation in 82Rb Cardiac PET/CT", A Thesis Submitted to the Faculty of Graduate Studies and Research Ottawa-Carleton Institute for Physics, 2010, 127 Pages.

* cited by examiner

SYSTEMS AND METHODS FOR EMISSION TOMOGRAPHY/COMPUTED TOMOGRAPHY DATA ACQUISITION

FIELD OF INVENTION

The technology disclosed herein generally relates to Emission Tomography (ET)/Computed Tomography (CT) data acquisition of a subject. More specifically, the technology discussed herein relates to optimizing the acquisition of CT data based on motion of the subject.

BACKGROUND

Emission Tomography (ET), for example, Positron Emission Tomography (PET) imaging, Single Photon Emission Computed Tomography (SPECT) imaging, and the like produces images of various biological processes and functions. In PET imaging, a solution including a tracer is injected into a subject (e.g., a human patient) to be scanned. The tracer is a pharmaceutical compound including a radioisotope with a relatively short half-life, for example, 18F-Fluoro-2-Deoxyglucose (FDG), which is a type of sugar that includes radioactive fluorine. The tracer may be adapted such that it is attracted to sites such as lesions within the subject, where specific biological or biochemical processes occur. Typically, the tracer moves towards and is taken up in one or more organs of the subject in which these biological and biochemical processes occur. For example, cancer cells may metabolize the tracer, allowing a PET scanner to create an image illuminating the cancerous region. Once the radioisotope decays, it emits a positron, which travels a short distance before annihilating with an electron. The short distance, also referred to as the positron range, is typically of the order of 1 mm for FDG in common subjects. The annihilation produces two high-energy photons propagating in substantially opposite directions.

PET imaging uses a photon detector array arranged around a scanning area, usually in a ring-shaped pattern, in which the subject or at least the part of interest of the subject is arranged. When the detector array detects the two photons within a short timing window, a so-called "coincidence" is recorded. A line connecting the two detectors that received the photons is called the Line Of Response (LOR). The reconstruction of a PET image is based on the premise that the decayed radioisotope is located somewhere on the LOR. The relatively short positron range may be neglected or may be compensated in the reconstruction. Each coincidence may be recorded in a list by three entries, wherein two entries represent the two detectors and one entry represents the time of detection. The coincidences in the list may be grouped in one or more sinograms. A sinogram is typically processed using image reconstruction algorithms to obtain volumetric images of the subject. However, PET imaging and SPECT imaging, typically fail to provide structural details of the subject as accurately as other types of scanners, for example, a Computed Tomography (CT) scanner, a Magnetic Resonance Imaging scanner, and the like.

A PET/CT scanner includes a CT scanner and a PET scanner installed around a single patient bore. A PET/CT scanner creates a fused volumetric image including a PET image spatially registered to a CT image. Similarly, a SPECT/CT scanner includes a SPECT scanner and a CT scanner installed around a single patient bore and creates a fused volumetric image including a SPECT image spatially registered to a CT image. PET/CT scanners and SPECT/CT scanners provide the advantage that the functional and biological features shown by the PET image or the SPECT image may be precisely located with respect to the structural details provided by the CT image.

In a typical ET/CT scan, the patient first undergoes a CT scan, and then the patient undergoes a ET scan before exiting the scanner. After the CT and ET data have been acquired, the ET/CT scanner processes the data and generates the fused ET/CT image. In order to generate quantitatively accurate ET images, the ET data needs to be corrected for several patient and system related factors. The most important patient related factor is the attenuation of the high-energy photons from an annihilation event, as they traverse through the patient body. In order to account for this effect, the CT data is used to compute the line attenuation co-efficients, a material dependent property, along the travel path of the high-energy photons. These attenuation co-efficients are used during the tomographic reconstruction of ET data.

Patient motion (e.g., motion due to respiration) is another factor in degrading the quantitative integrity of ET images. Respiratory motion may result in artifacts and/or contrast dilution of lesions due to motion blurring. Respiratory-gated acquisition of ET data may reduce motion blur. In a respiratory-gated acquisition, the ET data is partitioned during each respiratory cycle to produce independent ET images for each partition or gate. In order to generate quantitatively accurate ET images for each partition or gate, a corresponding CT image needs to be generated for attenuation correction.

Typically, the partitioning of ET and CT data is performed based on a respiratory curve produced by external motion monitoring devices, for example, camera based systems, pressure sensitive belts, pyrometers, and the like. However, such methods are disadvantageous since the external motion monitoring devices are expensive, complicate workflow and are cumbersome to use in a clinical setting. To overcome this, data-driven techniques have been developed to extract patient motion information from the ET and CT data. Such data driven techniques are disadvantageous as they cannot be applied in real-time and have to be applied retrospectively upon the completion of data acquisition.

An important consideration during the acquisition and partitioning of the CT data is the acquisition time of the CT data. The CT acquisition needs to be long enough to capture at least an entire respiratory cycle. However, since x-rays are harmful to the subject, the CT data acquisition should not be much longer than a respiratory cycle. When external motion monitoring device are used, an administrator of the ET/CT system analyzes a respiratory curve and prescribes an acquisition time for acquiring CT data. In addition to being cumbersome and expensive, methods based on external motion monitoring device may lead to a non-optimal acquisition time, since the prescribed acquisition time is subjective and dependent on the experience and perception of the administrator. Data-driven techniques based on CT data are also disadvantageous since the respiratory curve is not available a priori, in order to set an optimal acquisition time.

Thus, there is a need for an enhanced system and method for CT data acquisition.

BRIEF DESCRIPTION

In accordance with one aspect of the present technique, a method includes receiving Emission Tomography (ET) data of a subject from an ET/Computed Tomography (CT) scanner. The method further includes generating a first motion signal corresponding to a first bed position of the ET/CT scanner from the received ET data and determining whether the first motion signal indicates a periodic motion. The method also includes calculating a first time period of the first motion signal in response to determining that the first motion signal indicates the periodic motion and sending a first acquire notification to the ET/CT scanner to acquire Cinematographic (CINE) CT data from the first bed position based on the first time period.

In accordance with one aspect of the present system, a system includes a motion signal generator configured to receive ET data of a subject from an ET/CT scanner and generate a first motion signal corresponding to a first bed position of the ET/CT scanner from the received ET data. The system also includes a periodic motion analyzer configured to determine whether the first motion signal indicates a periodic motion and calculate a first time period from the first motion signal in response to determining that the first motion signal indicates the periodic motion. The system further includes a data acquisition module configured to send a first acquire notification to the ET/CT scanner to acquire CINE CT data from the first bed position based on the first time period.

In accordance with one aspect of the present technique, a method includes receiving Emission Tomography (ET) data of a subject from an ET/Computed Tomography (CT) scanner. The method further includes generating a first motion signal corresponding to a first bed position of the ET/CT scanner from the received ET data and determining whether the first motion signal indicates a periodic motion. The method also includes calculating a first time period of the first motion signal in response to determining that the first motion signal indicates the periodic motion and sending a first acquire notification to the ET/CT scanner to acquire Cinematographic (CINE) CT data from a second bed position based on the first time period.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

In the following specification and the claims, reference will be made to a number of terms, which shall be defined to have the following meanings.

The singular forms "a", "an", and "the" include plural references unless the context clearly dictates otherwise.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable, and include any computer program stored in memory for execution by devices that include, without limitation, mobile devices, clusters, personal computers, workstations, clients, and servers.

As used herein, the term "computer" and related terms, e.g., "computing device", are not limited to integrated circuits referred to in the art as a computer, but broadly refers to at least one microcontroller, microcomputer, programmable logic controller (PLC), application specific integrated circuit, and other programmable circuits, and these terms are used interchangeably herein.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Figure 1:
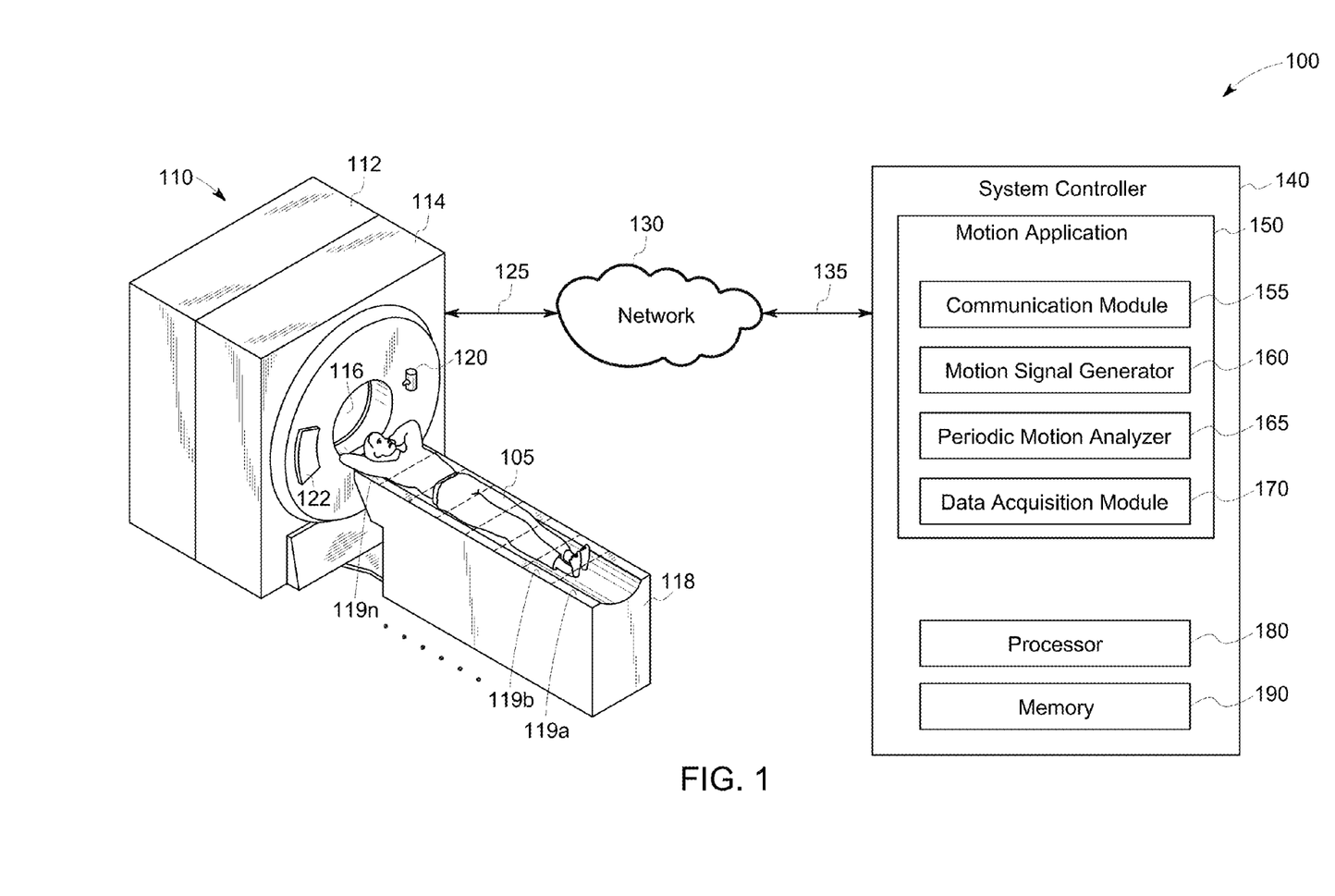
FIG. 1 is a block diagram illustrating an example of a system for Emission Tomography (ET)/Computed Tomography (CT) data acquisition of a subject.

A system and method for Computed Tomography (CT) data acquisition of a subject is described herein. FIG. 1 illustrates an exemplary block diagram of a system 100 for CT data acquisition. The system 100 includes an Emission Tomography (ET)/Computed Tomography (CT) scanner 110 and a system controller 140 that are operationally coupled via a network 130.

The network 130 may be a wired or wireless type, and may have any number of configurations such as a star configuration, token ring configuration, or other known configurations. Furthermore, the network 130 may include a local area network (LAN), a wide area network (WAN) (e.g., the internet), and/or any other interconnected data path across which multiple devices may communicate. In one embodiment, the network 130 may be a peer-to-peer network. The network 130 may also be coupled to or include portions of a telecommunication network for sending data in a variety of different communication protocols. In one embodiment, the network 130 may include Bluetooth communication networks or a cellular communications network for sending and receiving data such as via a short messaging service (SMS), a multimedia messaging service (MMS), a hypertext transfer protocol (HTTP), a direct data connection, WAP, email, or the like. The ET/CT scanner 110 and the system controller 140 are coupled to the network 130 via signal lines 125 and 135 respectively. The signal lines 125 and 135 are provided for illustrative purposes and represent the ET/CT scanner 110 and the system controller 140 communicating by wires or wirelessly over the network 130. While only one network 130 is shown coupled to the ET/CT scanner 110 and the system controller 140, multiple networks 130 may be coupled to the entities.

The ET/CT scanner 110 may be any type of scanner configured to scan a subject 105 (e.g., a human patient, an animal, and the like) and generate ET data and CT data of the subject 105. In the illustrated embodiment, the ET/CT scanner 110 is a Positron Emission Tomography (PET)/CT scanner 110 configured to generate PET data and CT data of the subject 105. Although FIG. 1 illustrates a PET/CT scanner 110 according to one embodiment, in another embodiment, the ET/CT scanner 110 may be a Single Photon Emission Computed Tomography (SPECT)/CT scanner configured to generate SPECT data and CT data of the subject 105. The PET/CT scanner 110 comprises a motorized bed 118 for disposing the subject 105 in a desired position for scanning. The motorized bed 118 comprises one or more bed positions 119a, 119b, and 119n that correspond to one or more anatomical regions of the subject 105. In FIG. 1 and the remaining figures, a letter after a reference number, for example, "119a" is a reference to the element having the particular reference number. A reference number in the text without a following letter, for example, "119" is a reference to any or all instances of the element bearing that reference number. During operation of the system 100, the motorized bed 118 is configured to move into an opening 116 created by a PET gantry 112 and a CT gantry 114 for generating the PET data and the CT data respectively.

The PET gantry 112 comprises one or more detectors (not shown) configured to detect photons emitted indirectly by a radioactive tracer in the subject 105 and generate PET data. In one embodiment, the PET gantry 112 generates list mode PET data that represents the functional and biological processes in the subject as a four dimensional (i.e., three spatial dimensions and a time dimension) image dataset. The CT gantry 114 comprises an X-ray source 120 configured to project an X-ray beam towards the subject 105. The CT gantry 114 further comprises an X-ray detector 122 configured to receive the X-ray beam attenuated by the subject 105 and generate CT data. The CT gantry 114 is configured to generate Cinematographic (CINE) CT data that represents the anatomical regions of the subject 105 as a four dimensional image data set. In one embodiment, the CT gantry 114 generates CINE CT data by instructing the X-ray source 120 and the X-ray detector 122 to rotate around the subject 105 and instructing the bed 118 to remain stationary. In another embodiment, the CT gantry 114 generates helical CT data by instructing the bed 118 to move slowly and instructing the X-ray detector 122 to cover an axial location for a time period. The time period is described in further detail with reference to the system controller 140. In such an embodiment, the CT gantry 114 further generates CINE CT data based on the helical CT data. The PET/CT scanner 110 is further configured to send the PET data and the CT data to the source controller 140 via the network 130.

The system controller 140 may be any type of device configured to receive PET data of a subject 105 from the PET/CT scanner 110 and optimize the acquisition of CT data based on the PET data. The system controller 140 includes a motion application 150, a processor 180, and a memory 190. The motion application 150 includes a communication module 155, a motion signal generator 160, a periodic motion analyzer 165, and a data acquisition module 170. The plurality of modules of the respiratory application 150, the processor 180, and the memory 190 are coupled to a bus (not shown) for communication with each other. Although, one system controller 140 is shown in FIG. 1, a plurality of system controllers 140 may be coupled to the network 130.

The processor 180 may include at least one arithmetic logic unit, microprocessor, general purpose controller or other processor arrays to perform computations, and/or retrieve data stored on the memory 190. In one embodiment, the processor 180 may be a multiple core processor. The processor 180 processes data signals and may include various computing architectures including a complex instruction set computer (CISC) architecture, a reduced instruction set computer (RISC) architecture, or an architecture implementing a combination of instruction sets. In one embodiment, the processing capability of the processor 180 may be limited to supporting the retrieval of data and transmission of data. In another embodiment, the processing capability of the processor 180 may also perform more complex tasks, including various types of feature extraction, modulating, encoding, multiplexing, and the like. Other type of processors, operating systems, and physical configurations are also envisioned.

In one embodiment, the memory 190 may be a non-transitory storage medium. For example, the memory 190 may be a dynamic random access memory (DRAM) device, a static random access memory (SRAM) device, flash memory or other memory devices. The memory 190 may also include a non-volatile memory or similar permanent storage device, and media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. The memory 190 stores data that is required for the motion application 150 to perform associated functions. In some embodiments, the memory 190 stores the modules (e.g., communication module 155, the periodic motion analyzer 165, and the like) of the motion application 150. In some embodiments, the memory 190 stores a number of bed positions and one or more signal thresholds, defined by, for example, an administrator of the system controller 140 based on previously generated clinical data. The signal thresholds and the number of bed positions are described in further detail with reference to the periodic motion analyzer 165 and the data acquisition module 170.

The communication module 155 includes codes and routines configured to handle communications between the PET/CT scanner 110 and the modules of the motion application 150. In one embodiment, the communication module 155 includes a set of instructions executable by the processor 180 to provide the functionality for handling communications between the PET/CT scanner 110 and the modules of the motion application 150. In another embodiment, the communication module 155 is stored in the memory 190 and is accessible and executable by the processor 180. In either embodiment, the communication module 155 is adapted for communication and cooperation with the processor 180 and other modules of the motion application 150.

In one embodiment, the communication module 155 receives list mode PET data of a subject 105 from the PET/CT scanner 110 via the network 120. In such an embodiment, the communication module 155 sends the list mode PET data to the motion signal generator 160. In another embodiment, the communication module 155 receives a motion signal from the motion signal generator 160. In such an embodiment, the communication module 155 sends the PET data and the motion signal to, for example, a display device (not shown) configured to display the PET data and the motion signal to an administrator of the system controller 140. In yet another embodiment, the communication module 150 receives a notification from the data acquisition module 170. In such an embodiment, the communication module 155 sends the notification to the PET/CT scanner 110. The motion signal and the notification are described below in further detail with reference to the motion signal generator 160 and data acquisition module 170 respectively.

The motion signal generator 160 includes codes and routines configured to receive list mode PET data and generate one or more motion signals. In one embodiment, the motion signal generator 160 includes a set of instructions executable by the processor 180 to provide the functionality for receiving list mode PET data and generating one or more motion signals. In another embodiment, the motion signal generator 160 is stored in the memory 190 and is accessible and executable by the processor 180. In either embodiment, the motion signal generator 160 is adapted for communication and cooperation with the processor 180 and other modules of the motion application 150.

The motion signal generator 160 receives list mode PET data of a subject 105 from the PET/CT scanner 110. The motion signal generator 160 then generates one or more motion signals from the received list mode PET data corresponding to one or more bed positions 119. The motion signal may include signals indicating at least one of a respiratory and a cardiac motion of the subject 105. In one embodiment, the motion signal generator 160 generates the motion signal based on a data driven gating technique using a multivariate data analysis for example, principal component analysis, independent component analysis, and the like. In such an embodiment, the motion signal generator 160 generates average time information for each set of sinograms in the received list mode PET data. The motion signal generator 160 subtracts the average time information from the list mode PET data to generate zero mean information for each set of sinograms. The motion signal generator 160 then generates a motion signal corresponding to a bed position 119 by performing, for example, principal component analysis on the zero mean information. An exemplary data driven gating technique is described in further detail in commonly assigned U.S. 20120281897, filed on 3 May 2012 and is herein incorporated by reference in entirety.

The motion signal generator 160 is further configured to send the one or more motion signals corresponding to the one or more bed positions 119 to the periodic motion analyzer 165. In one embodiment, motion signal generator 160 also generates graphical data for displaying the list mode PET data and the one or more motion signals to, for example, an administrator of the system controller 140. In such an embodiment, the motion signal generator 160 sends the graphical data to a display device (not shown) coupled to the system controller 140. The display device (not shown) renders the graphical data and displays the one or more motion signals.

The periodic motion analyzer 165 includes codes and routines configured to determine whether a motion signal indicates periodic motion (i.e., respiratory and/or cardiac motion of the subject 105). In one embodiment, the periodic motion analyzer 165 includes a set of instructions executable by the processor 180 to provide the functionality for determining whether a motion signal indicates periodic motion. In another embodiment, the periodic motion analyzer 165 is stored in the memory 190 and is accessible and executable by the processor 180. In either embodiment, the periodic motion analyzer 165 is adapted for communication and cooperation with the processor 180 and other modules of the motion application 150.

The periodic motion analyzer 165 determines whether the one or more motion signals received from the motion signal generator 160 indicate a periodic motion. In one embodiment, the periodic motion analyzer 165 computes one or more signal metrics of a motion signal in, for example, a respiratory frequency band, a cardiac frequency band, and the like, using a band pass filter. The band pass filter is configured to remove signals that have frequencies outside the respiratory frequency band and/or the cardiac frequency band in the received motion signal. The respiratory frequency band may be defined by for example, an administrator of the system controller 140 based on a typical respiratory rate (e.g., 20-40 breaths per minute) of a subject 105. Similarly, the cardiac frequency band may be defined by, for example, an administrator of the system controller 140 based on a typical cardiac rate (e.g., 70-90 beats per minute) of a subject 105. The one or more signal metrics include, for example, a fractional power within a typical motion frequency band, ratio of peak amplitude within a typical motion frequency band to mean amplitude outside the typical motion frequency band, a correlation factor with a typical motion signal, etc. The periodic motion analyzer 165 then determines whether the motion signal indicates periodic motion by determining whether the one or more signal metrics exceed the one or more signal thresholds. The one or more signal thresholds include, for example, a respiratory power threshold, a cardiac power threshold, a respiratory amplitude threshold, a cardiac amplitude threshold, a respiratory correlation threshold, and a cardiac correlation threshold.

In one embodiment, the periodic motion analyzer 165 computes a fractional power of the motion signal within the respiratory frequency band. The periodic motion analyzer 165 then determines whether the fractional power of the motion signal exceeds the respiratory power threshold stored in the memory 190. The periodic motion analyzer 165 infers that the motion signal indicates a respiratory motion if the fractional power exceeds a respiratory power threshold. Similarly, the periodic motion analyzer 165 infers that the motion signal indicates a cardiac motion if the fractional power of the motion signal within a cardiac frequency band exceeds a cardiac power threshold. The fractional power of the motion signal is described below in further detail with reference to FIG. 3.

In another embodiment, the periodic motion analyzer 165 computes a peak amplitude of the motion signal within the respiratory frequency band. The periodic motion analyzer 165 then determines whether the peak amplitude of the motion signal exceeds the respiratory amplitude threshold stored in the memory 190. The periodic motion analyzer 165 infers that the motion signal indicates a respiratory motion if the peak amplitude exceeds a respiratory amplitude threshold. Similarly, the periodic motion analyzer 165 infers that the motion signal indicates a cardiac motion if the peak amplitude of the motion signal within a cardiac frequency band exceeds a cardiac amplitude threshold.

In another embodiment, the periodic motion analyzer 165 computes a correlation factor of the motion signal within the respiratory frequency band based on, for example, the similarity between the motion signal and a standard respiratory signal. The periodic motion analyzer 165 then determines whether the correlation factor of the motion signal exceeds the respiratory correlation threshold stored in the memory 190. The periodic motion analyzer 165 infers that the motion signal indicates a respiratory motion if the correlation factor exceeds the respiratory correlation threshold. Similarly, the periodic motion analyzer 165 computes a correlation factor of the motion signal within a cardiac frequency band based on the similarity of the motion signal to a standard cardiac signal. The periodic motion analyzer 165 infers that the motion signal indicates a cardiac motion if the correlation factor of the motion signal within a cardiac frequency band exceeds a cardiac correlation threshold. In such an embodiment, the standard respiratory and/or cardiac signals may be defined and stored in the memory 190 by, for example, an administrator of the system controller 140 based on previously generated clinical data.

In any of the above embodiments, the periodic motion analyzer 165 sends a message to the data acquisition module 170 stating that the motion signal corresponding to a bed position 119 either indicates periodic motion or fails to indicate periodic motion. If the motion signal corresponding to a bed position 119 indicates periodic motion, the periodic motion analyzer 165 is further configured to determine a time period from the motion signal and send it to the data acquisition module 170. The time period is the amount of time required to complete at least one full cycle in a periodic signal. For example, the a time period of a motion signal indicating respiratory motion is the amount of time taken by the subject 105 to complete one cycle of inhalation and exhalation. In one embodiment, the time period is the amount of time required to complete half a cycle in a period signal. For example, the time period of a motion signal indicating respiratory motion is the amount taken by the subject 105 to complete inhalation or exhalation alone.

The data acquisition module 170 includes codes and routines configured to send one or more notifications to the PET/CT scanner 110 to acquire CINE CT data of the subject 105. In one embodiment, the data acquisition module 170 includes a set of instructions executable by the processor 180 to provide the functionality for sending one or more notifications to the PET/CT scanner 110. In another embodiment, the data acquisition module 170 is stored in the memory 190 and is accessible and executable by the processor 180. In either embodiment, the data acquisition module 170 is adapted for communication and cooperation with the processor 180 and other modules of the motion application 150.

In one embodiment, the data acquisition module 170 receives a time period and a message stating that a motion signal corresponding to, for example, bed position 119b indicates periodic motion. In such an embodiment, the data acquisition module 170 sends an acquire notification to the PET/CT scanner 110. The acquire notification instructs the PET/CT scanner 110 to acquire CINE CT data of the subject 105 from the bed position 119b for a duration based on the time period. In another embodiment the data acquisition module 170 receives a message stating that a motion signal corresponding to, for example, bed position 119b fails to indicate periodic motion. In such an embodiment, the data acquisition module 170 sends a cancel notification to the PET/CT scanner 110. The cancel notification instructs the PET/CT scanner 110 to prevent the acquisition of CINE CT data of the subject 105 from the bed position 119b. In a further embodiment, in addition to preventing the acquisition of CINE CT data, the cancel notification also instructs the PET/CT scanner 110 to acquire helical CT data with fast bed movement of the subject 105 from the bed position 119b.

In one embodiment where the motion signal generator generates graphical data for displaying the motion signal to, for example, an administrator of the system 100, the data acquisition module 170 receives a user input from the administrator. In such an embodiment, the administrator may manually determine whether the motion signal indicates a periodic motion and provides the user input. For example, the administrator provides a user input via a user interface instructing the data acquisition module 170 for sending an acquire notification to the PET/CT scanner 110 in response to determining that the motion signal corresponding to bed position 119b indicates a periodic motion. In such an example, the data acquisition module 170 sends the acquire notification based on the time period calculated by the periodic motion analyzer 165 or the time period calculated and provided by the administrator in the user input. In another example, the administrator provides a user input via the user interface instructing the data acquisition module 170 for sending a cancel notification to the PET/CT scanner 110 in response to determining that the motion signal corresponding to the bed position 119b fails to correspond to the periodic motion.

In any of the above embodiments, the data acquisition module 170 is further configured to determine whether the bed position is the final bed position of the PET/CT scanner 110 based on the total number of bed positions stored in the memory 180. For example, if the bed position 119b is not the final bed position, the data acquisition module 170 requests the motion signal generator 160 to generate a motion signal corresponding to, for example, the next bed position 119n of the PET/CT scanner 110. If the bed position 119b is the final bed position of the PET/CT scanner 110, the data acquisition module 170 sends an instruction to, for example, an image reconstruction module (not shown) to receive the CINE CT data corresponding to one or more bed positions 119 from the PET/CT scanner 110 and reconstruct one or more CT images of the subject 105.

The motion application 150 is advantageous since it reduces the x-ray dosage on the subject 105 by instructing the PET/CT scanner 110 to acquire CINE CT data in real-time and only from bed positions 119 that indicate periodic motion (i.e., respiratory and/or cardiac motion). Furthermore, the motion application 150 is advantageous since it optimizes the duration for which the subject 105 is exposed to X-rays without compromising on the quality of the reconstructed CT and PET images by instructing the PET/CT scanner 110 to acquire CINE CT data for each bed position 119 based on the corresponding time period. Although in FIG. 1 and the remainder of the application, the ET/CT scanner 110 is described as PET/CT scanner 110 according to one embodiment, in another embodiment the ET/CT scanner 110 may be a SPECT/CT scanner 110. In such an embodiment, the SPECT/CT scanner 110 is configured to generate and send SPECT data to the system controller 140. The system controller 140 receives the SPECT data of the subject 105 and optimizes the acquisition of CT data based on the SPECT data. In such an embodiment, the motion application 150 generates a motion signal from the SPECT data and determines whether the motion signal indicates a periodic motion.

Figure 2:
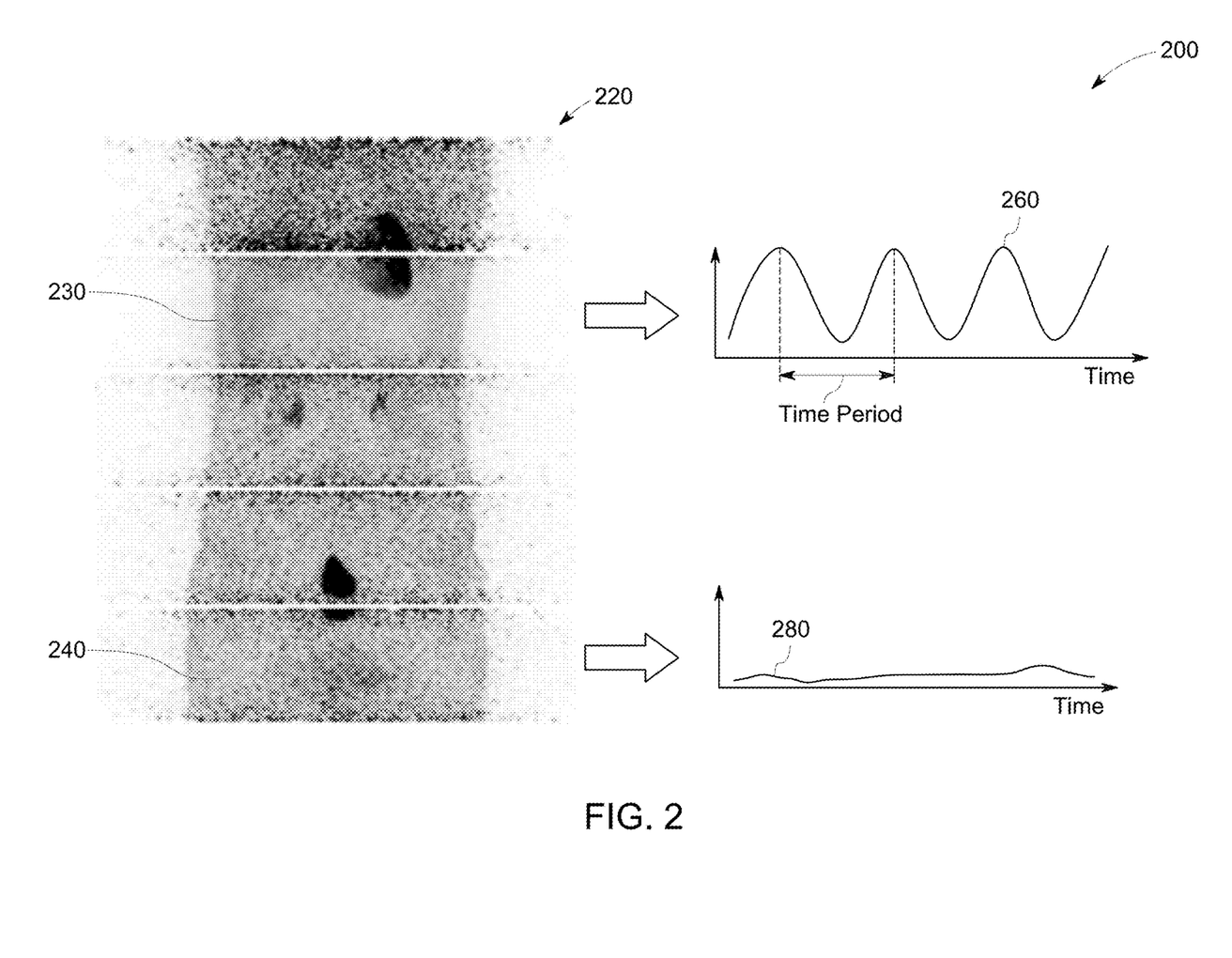
FIG. 2 is a graphical representation illustrating example motion signals and PET data.

Referring now to FIG. 2, an exemplary graphical representation 200 of list mode PET data and motion signals is illustrated. The graphical representation 200 comprises list mode PET data 220 of a subject corresponding to a plurality of bed positions. Although, the list mode PET data 220 received by the system controller is four dimensional, FIG. 2 illustrates the list mode PET data 220 as a two dimensional image for simplicity and convenience. The graphical representation 200 further comprises motion signals 260 and 280 generated by the motion signal generator from the list mode PET data 220 corresponding to bed positions 230 and 240 respectively. The motion signals 260 and 280 are represented as graphs wherein the x-axis represents time and the y-axis represents the amplitude of the motion signal. Although, the motion signal generator is configured to generate motion signals for list mode PET data 220 corresponding to all bed positions, FIG. 2 illustrates only two motion signals 230 and 240 for simplicity and convenience.

Figure 3:
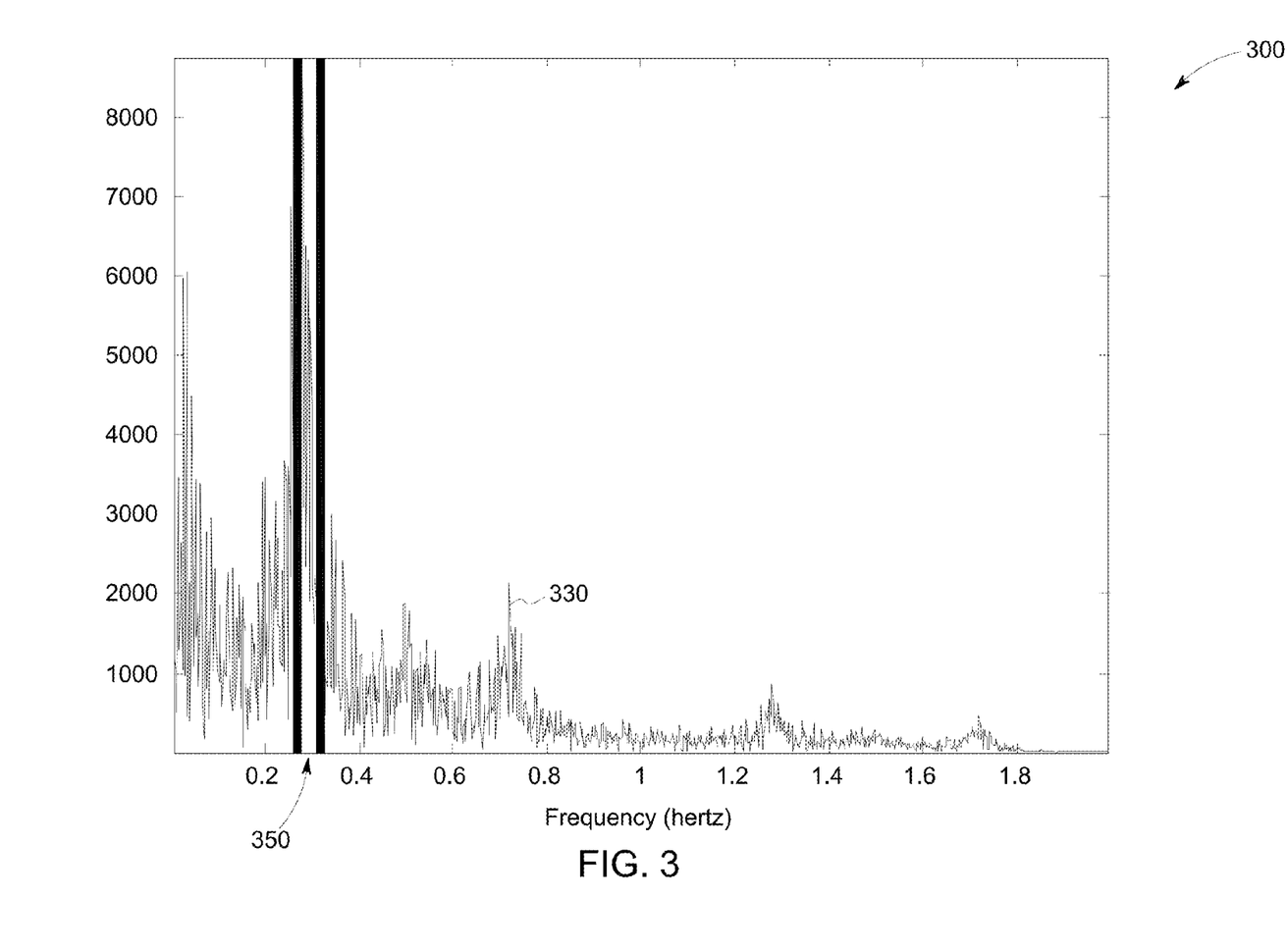
FIG. 3 is a graphical representation illustrating an example of a motion signal in a frequency domain.

Referring now to FIG. 3, an exemplary graphical representation 300 of a motion signal 330 in a frequency domain spectrum is illustrated. The motion signal 330 is represented as a graph 300 wherein the x-axis represents frequency (hertz) and the y-axis represents the amplitude of the motion signal 330. In the illustrated example, the periodic motion analyzer determines that the motion signal 330 indicates respiratory motion, since the fractional power of the motion signal 330 within the respiratory frequency band 350 (0.25 hertz-0.30 hertz) exceeds a respiratory power threshold. In the illustrated example, the administrator of the system controller defines the respiratory power threshold as 25% of the power of the motion signal 330 in all frequencies.

Figure 4:
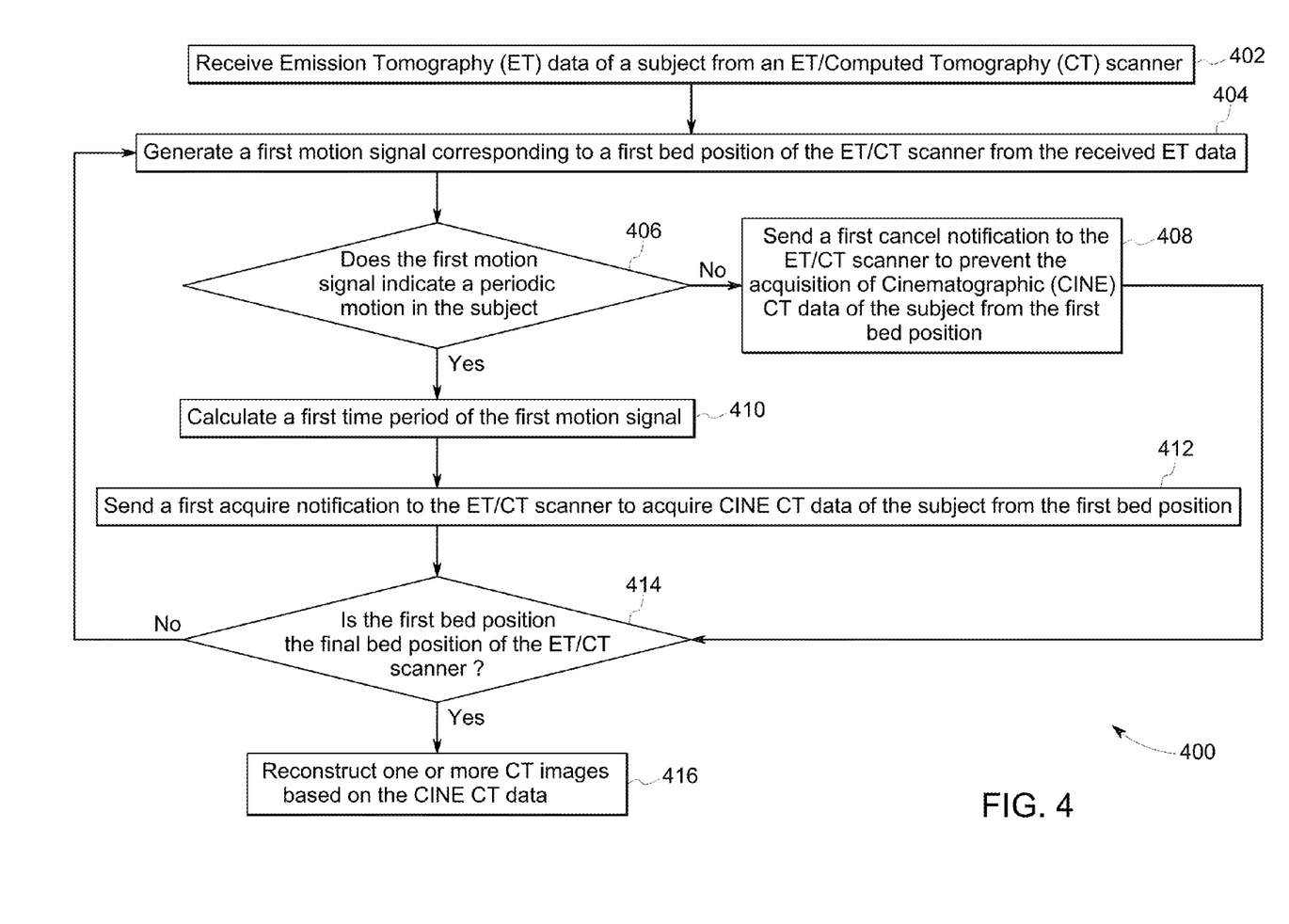
FIG. 4 is a flow diagram illustrating an example of a method for ET/CT data acquisition of a subject.

FIG. 4 is a flow diagram illustrating an example method 400 for ET/CT data acquisition of a subject. The motion signal generator receives ET data of a subject from an ET/CT scanner 402. For example, the motion signal generator receives PET data from a PET/CT scanner. In another example, the motion signal generator receives SPECT data from a SPECT/CT scanner. The motion signal generator then generates a first motion signal corresponding to a first bed position of the ET/CT scanner from the received ET data 404. For example, the motion signal generator generates a first motion signal 260 (See, FIG. 2) corresponding to list mode ET data received from a first bed position 230 (See, FIG. 2) based on a data driven gating technique. The periodic motion analyzer determines whether the first motion signal indicates a periodic motion in the subject 406. If the first motion signal indicates periodic motion, the motion signal generator calculates a first time period from the first motion signal 410. For example, the periodic motion analyzer determines that the first motion signal 260 (See, FIG. 2) indicates respiratory motion and calculates a first time period of the first motion signal. The data acquisition module then sends a first acquire notification to the ET/CT scanner to acquire CINE CT data of the subject from the first bed position based on the first time period 412. If the first motion signal fails to indicate periodic motion, the data acquisition module sends a first cancel notification to the ET/CT scanner to prevent the acquisition of CINE CT data of the subject from the first bed position 408. In a further embodiment, the first cancel notification further instructs the ET/CT scanner to acquire helical CT data of the subject from the first bed position in addition to preventing the acquisition of CINE CT data. In such an embodiment, the first motion signal fails to indicate periodic motion and an acquisition protocol of the ET/CT scanner might not have prescribed the acquisition of, for example, a full body helical CT data of the subject prior to the acquisition of ET data.

The data acquisition module then determines whether the first bed position is the final bed position of the ET/CT scanner 414. If the first bed position is the final bed position, the data acquisition module sends an instruction to reconstruct one or more CT images based on the acquired CINE CT data 416. If the first bed position is not the final bed position, the data acquisition module sends a request to the motion signal generator. The motion application then repeats the method 400 from step 404 until the ET data and the motion signals from all the bed positions are analyzed by the motion application. For example, the motion signal generator receives the request and generates a second motion signal corresponding to a second bed position of the ET/CT scanner from the received ET data 404. The periodic motion analyzer determines whether the second motion signal indicates a periodic motion in the subject 406. If the second motion signal indicates periodic motion, the motion signal calculates a second time period of the second motion signal 410. The data acquisition module then sends a second acquire notification to the ET/CT scanner to acquire CINE CT data of the subject from the second bed position based on the second time period 412. In one embodiment, the data acquisition module sends the second acquire notification to the ET/CT scanner to acquire CINE CT data of the subject from the second bed position based on the first time period. In such an embodiment, the periodic motion analyzer fails to calculate the second time period as it infers that the time period (e.g., respiratory time period of a subject) calculated at the first bed position is the same at the second bed position. The data acquisition module then determines whether the second bed position is the final bed position of the ET/CT scanner 414. The method 400 stops by reconstructing one or more CT images based on the CINE CT data received from the first and the second bed positions, if the second bed position is the final bed position of the ET/CT scanner.

Figure 5:
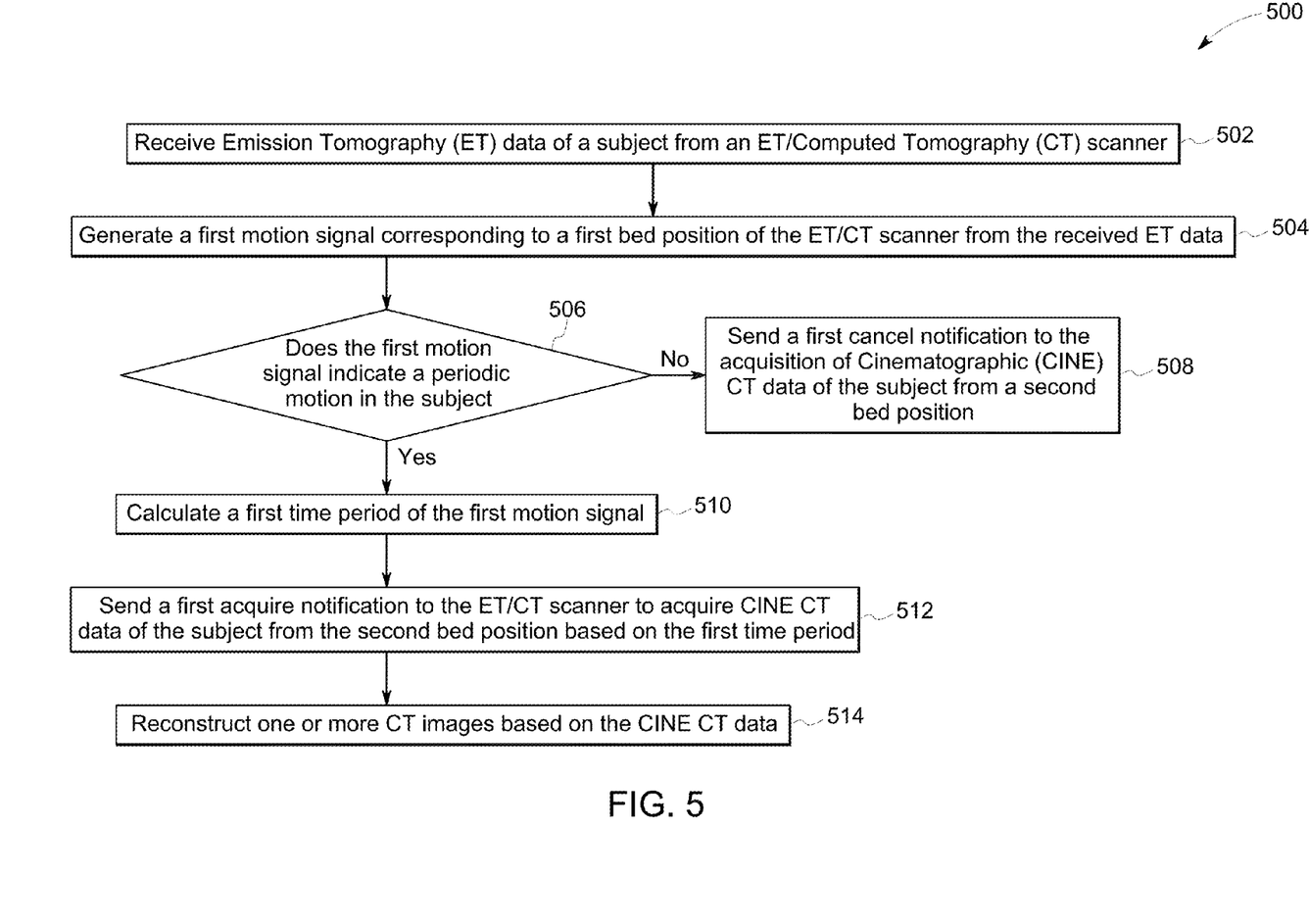
FIG. 5 is a flow diagram illustrating an example of another method for ET/CT data acquisition.

FIG. 5 is a flow diagram illustrating another exemplary method 500 for ET/CT data acquisition of a subject. The motion signal generator receives ET data of a subject from an ET/CT scanner 502. The motion signal generator then generates a first motion signal corresponding to a first bed position of the ET/CT scanner from the received ET data 504. For example, the motion signal generator generates a first motion signal from ET data received from a first bed position that corresponds to the diaphragm region of the subject. The periodic motion analyzer determines whether the first motion signal indicates a periodic motion in the subject 506. If the first motion signal indicates periodic motion, the motion signal generator calculates a first time period from the first motion signal 510. For example, the periodic motion analyzer determines that the first motion signal indicates respiratory motion and calculates a first time period of the first motion signal.

The data acquisition module then sends a first acquire notification to the ET/CT scanner to acquire CINE CT data of the subject from a second bed position based on the first time period 512. In the above example, the data acquisition module sends the acquire notification for acquiring CINE CT data from a second bed position that corresponds to the lung region of the subject based on the first time period. This is advantageous in scenarios wherein, for example, the quality of the ET data corresponding to the second bed position (i.e., the lung region of the subject) is low. In such an example, the low quality of the ET data might lead to an erroneous determination of whether the ET data corresponding to the second bed position indicates periodic motion. If the first motion signal fails to indicate periodic motion, the data acquisition module sends a first cancel notification to the ET/CT scanner to prevent the acquisition of CINE CT data of the subject from the second bed position 508. The method 500 stops by reconstructing one or more CT images based on the CINE CT data received from the second bed position.

In FIGS. 4-5 and the remainder of the application, the terms a first bed position and a second bed position are used to distinctly refer to any two bed positions of the ET/CT scanner and not necessarily refer only to the first two bed positions of the ET/CT scanner that are located next to each other. For example, in one embodiment, the first and the second bed positions could refer to bed positions 119b and 119n (See, FIG. 1) respectively. In another embodiment, the first and the second bed positions could refer to bed positions 119a and 119b (See, FIG. 1) respectively. In yet another embodiment, the first and the second bed positions could refer to bed positions 119b and 119a (See, FIG. 1) respectively.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the technology has been described in detail in connection with only a limited number of embodiments, it should be readily understood that the invention is not limited to such disclosed embodiments. Rather, the technology can be modified to incorporate any number of variations, alterations, substitutions or equivalent arrangements not heretofore described, but which are commensurate with the spirit and scope of the disclosure. Additionally, while various embodiments of the technology have been described, it is to be understood that aspects of the technology may include only some of the described embodiments. Accordingly, the inventions are not to be seen as limited by the foregoing description, but are only limited by the scope of the appended claims.

What is claimed as new and desired to be protected by Letters Patent of the United States is:

1. A method for optimizing Computed Tomography (CT) data acquisition, the method comprising:
    receiving Emission Tomography (ET) data of a subject from an ET/CT scanner;
    generating a first motion signal corresponding to a first bed position of the ET/CT scanner from the received ET data using a data driven gating technique;
    determining whether the first motion signal indicates a periodic motion;
    calculating a first time period of the first motion signal in response to determining that the first motion signal indicates the periodic motion; and
    sending a first acquire notification to the ET/CT scanner to acquire Cinematographic (CINE) CT data from the first bed position based on the first time period.

2. The method of claim 1, further comprising sending a first cancel notification to prevent the acquisition of CINE CT data from the first bed position of the ET/CT scanner in response to determining that the first motion signal fails to indicate the periodic motion.

3. The method of claim 1, further comprising computing a signal metric of the first motion signal in at least one of a respiratory frequency band and a cardiac frequency band.

4. The method of claim 3, wherein determining whether the first motion signal indicates a periodic motion further comprises determining whether the signal metric of the first motion signal exceeds a signal threshold.

5. The method of claim 1 further comprising:
    generating graphical data for displaying the first motion signal to an administrator of the ET/CT scanner; and
    receiving a user input for sending the first acquire instruction to the ET/CT scanner from the administrator in response to the administrator determining that the first motion signal indicates the periodic motion.

6. The method of claim 1, further comprising determining whether the first bed position is a final bed position of the ET/CT scanner.

7. The method of claim 6, further comprising:
    generating a second motion signal corresponding to a second bed position of the ET/CT scanner from the received ET data in response to determining that the first bed position is not the final bed position;
    determining whether the second motion signal indicates the periodic motion;
    calculating a second time period of the second motion signal in response to determining that the second motion signal indicates the periodic motion; and
    sending a second acquire notification to the ET/CT scanner to acquire CINE CT data from the second bed position based on the second time period.

8. The method of claim 1, further comprising sending a first cancel notification to prevent the acquisition of CINE CT data from the second bed position of the ET/CT scanner in response to determining that the first motion signal fails to indicate the periodic motion.

9. A system including an Emission Tomography (ET)/Computed Tomography (CT) scanner configured to scan a subject and generate ET data and Cinematographic (CINE) CT data of the subject, and a system controller operationally coupled to the ET/CT scanner, the system controller comprising:
    at least one processor;
    a motion signal generator stored in a memory and executable by the at least one processor, the motion signal generator configured to receive ET data of the subject from the ET/CT scanner and generate a first motion signal corresponding to a first bed position of the ET/CT scanner from the received ET data using a data driven gating technique;
    a periodic motion analyzer stored in the memory and executable by the at least one processor, the periodic motion analyzer communicatively coupled with the motion signal generator configured to determine whether the first motion signal indicates a periodic motion and calculate a first time period of the first motion signal in response to determining that the first motion signal indicates the periodic motion; and
    a data acquisition module stored in the memory and executable by the at least one processor, the data acquisition module communicatively coupled with the periodic motion analyzer configured to send a first acquire notification to the ET/CT scanner to acquire CINE CT data from the first bed position based on the first time period.

10. The system of claim 9, wherein the data acquisition module is further configured to send a first cancel notification to prevent the acquisition of CINE CT data from the first bed position of the ET/CT scanner in response to determining that the first motion signal fails to indicate the periodic motion.

11. The system of claim 9, wherein the periodic motion analyzer is further configured to compute a signal metric of the first motion signal in at least one of a respiratory frequency band and a cardiac frequency band and determine whether the signal metric exceeds a signal threshold.

12. The system of claim 9, wherein the motion signal generator is further configured to generate graphical data for displaying the first motion signal generator to an administrator of the ET/CT scanner.

13. The system of claim 12, wherein the data acquisition module is further configured to receive a user input for sending the first acquire instruction to the ET/CT scanner from the administrator in response to the administrator determining that the first motion signal indicates the periodic motion.

14. The system of claim 9, wherein the data acquisition module is further configured to determine whether the first bed position is a final bed position of the ET/CT scanner.

15. The system of claim 14, wherein the motion signal generator is further configured to generate a second motion signal corresponding to a second bed position of the ET/CT scanner from the received ET data in response to determining that the first bed position is not the final bed position.

16. A method for optimizing Computed Tomography (CT) data acquisition, the method comprising:

receiving Emission Tomography (ET) data of a subject from an ET/CT scanner;

generating a first motion signal corresponding to a first bed position of the ET/CT scanner from the received ET data using a data driven gating technique;

determining whether the first motion signal indicates a periodic motion;

calculating a first time period of the first motion signal in response to determining that the first motion signal indicates the periodic motion; and     sending a first acquire notification to the ET/CT scanner to acquire Cinematographic (CINE) CT data from a second bed position based on the first time period.

17. The method of claim 16, further comprising determining a fractional power of the first motion signal in at least one of a respiratory frequency band and a cardiac frequency band.

18. The method of claim 17, further comprising determining whether the fractional power of the first motion signal exceeds at least one of a respiratory power threshold and a cardiac power threshold.

* * * * *